United States Patent [19]

Stadler née Szoke et al.

[11] Patent Number: 4,826,963

[45] Date of Patent: May 2, 1989

[54] INCLUSION COMPLEX OF 7-ISOPROPOXY-ISOFLAVON FORMED WITH CYCLODEXTRIN, THE PREPARATION THEREOF AND PHARMACEUTICAL COMPOSITIONS CONTAINING THESE COMPOUNDS AS ACTIVE INGREDIENT

[75] Inventors: Ágnes Stadler née Szőke; József Szejtli; Viktor Weiszfeiler; Zoltán Vargay; Katalin Kálóy; Vera Gergely; Tamás Szüts, all of Budapest, Hungary

[73] Assignee: Chinoin Gyogyszer es Vegyeszeti Termekek Gyara, R.T., Budapest, Hungary

[21] Appl. No.: 905,837

[22] Filed: Sep. 10, 1986

[30] Foreign Application Priority Data

Sep. 10, 1985 [HU] Hungary ............................. 3415/85

[51] Int. Cl.⁴ .............................................. C08B 37/16
[52] U.S. Cl. .................................................... 536/103
[58] Field of Search ........................... 549/403; 536/46

[56] References Cited

U.S. PATENT DOCUMENTS 3,949,085 4/1976 Feuer et al. ......................... 514/456

4,599,327 7/1986 Nógrádi et al. ....................... 514/58

OTHER PUBLICATIONS

Frömming, "Cyclodextrin in Pharmaceutical Industry", -Proceedings of the First International Symposium on Cyclodextrins, Ed. J. Szejtli, D. Rgidel Publishing Co., London, England, 1981, pp. 367-376.
Controlled Drug Bioavailability, vol. 3, Edited by Victor F. Smolen and Luann Ball, John Wiley & Sons, pp. xii, xiii, Oct. 1984, Chapter 8, Molecular Entrapment and Release Properties of Drugs by Cyclodextrins J. Szejtli, pp. 365–421, (New York 1985).

Primary Examiner—Nicky Chan
Attorney, Agent, or Firm—Herbert Dubno; Jonathan Myers

[57] ABSTRACT

The invention relates to the inclusion complexes of 7-isopropoxy-isoflavone formed with cyclodextrin or cyclodextrin derivatives as well as to the pharmaceutical compositions containing these inclusion complexes as active ingredient. The invention further relates to the preparation of the new inclusion complexes. The new inclusion complex according to the invention shows higher dissolution and resorption properties as compared to the active ingredient administered per se.

1 Claim, No Drawings

INCLUSION COMPLEX OF 7-ISOPROPOXY-ISOFLAVON FORMED WITH CYCLODEXTRIN, THE PREPARATION THEREOF AND PHARMACEUTICAL COMPOSITIONS CONTAINING THESE COMPOUNDS AS ACTIVE INGREDIENT

The invention relates to an inclusion complex of 7-isopropoxy-isoflavone formed with any cyclodextrin. In the inclusion complex according to the invention α-, β- or γ-cyclodextrin, heptakis-2,6-O-dimethyl- or heptakis-2,3,6-tri-O-methyl-β-cyclodextrin or any water-soluble β-cyclodextrin polymer having a molecular weight of about 10,000, can be used as the cyclodextrin component.

Further, the invention relates to a pharmaceutical composition containing the inclusion complex of 7-isopropoxy-isoflavone formed with any cyclodextrin derivative as an active ingredient.

From the orally administered pharmaceutical composition according to the invention Ipriflavon (7-isopropoxy-isoflavone) is resorbed in a pharmacologically active concentration in not metabolized form and can be detected in the blood.

The preparation of the Ipriflavon is described in the GB Patent Specification No. 1,360,461 and the characteristics of the compound are the following molecular weight: 280.3; melting point: 112°–118° C.; solubility in water at 25° C.: 1–2 μg/ml. It is poorly soluble in acetone but dissolves well in chloroform and in dimethyl formamide.

The known tablet Yambolap containing 200 mg of Ipriflavon as an active ingredient is used for the treatment of osteoporosis and osteomalacia. However, due to its bad solubility and resorption the therapeutical effects thereof are not satisfactory.

Administering the radioactive labelled Ipriflavon to beagle dogs and detecting the amount of the radioactive material discharged, it has been observed that only the 12% of the radioactive material administered are discharged with the urine. The HPLC analysis of the blood has shown that the metabolites thereof (7-hydroxy-isoflavone as main metabolite) appear in the blood.

Different efforts have been made to increase the resorption of Ipriflavon and the main metabolite (7-hydroxy-isoflavone) thereof. In the European Patent Specification No. 0129893 it is disclosed that the resorption and solubility of pharmaceutical compositions having poor solubility increase if they are ground together with inert carriers. For example 2 g of Ipriflavon were ground for 10–60 minutes together with 2 g of aerosil or 2 g of active carbon or 2 g of activated clay or 2 g of activated alumina in a vibrating mill using steel balls. The solubility of the product obtained, e.g. with aerosil, was 20.4 μg/ml in 50% aqueous methanol after 30 minutes at 37° C., while the solubility of the unground mixture was only 15.0 μg/ml, accordingly a 1.36-fold increase of the vitro dissolution capability was achieved. Analyzing the blood-levels by dogs after oral administration, Ipriflavon cannot be detected in the blood. The grinding together with aerosil increases the resorption of the main metabolite from 0.152 μg.hr/ml to 0.485 μg.hr/ml which corresponds to a 3.19-fold increase.

It is well-known that that the different unstable and volatile active ingredients of the different pharmaceutical compositions and pesticides become stable and crystalline when forming "molecular capsules" with cyclodextrin. From a pharmaceutical point of view the most important effect is that the inclusion complexes of the different active ingredients with poor solubility in water, become wettable with water, they can easily be dispersed and they dissolve in water easily. Their solubility and resorption is generally 1.3–3-fold higher than that of the free, uncomplexed active ingredients (W. F. Smolen and L. A. Ball: Controlled drug bioavailability, Vol. 3., page 365, John Wiley, N.Y., 1985).

Surprisingly we found that after administering the inclusion complex according to the invention, the in vitro solubility of Ipriflavon is 10-fold and the blood-level of the main metabolite is 15–20-fold higher than that of the Ipriflavon administered per se. The resorption of Ipriflavon in an unchanged form and in pharmaceutically effective concentration can be realized as well.

The cyclodextrins are prepared from starches using cyclodextrin-glucosil transferase enzyme. There exists three different kinds of cyclodextrin, i.e. the α-, β- and γ-cyclodextrin which consist of 6,7 or 8 glucopiranose units connected with α-1,4 glucosidic bonds. The three cyclodextrins differ from each other in molecular weight, water-solubility and in hollow-diameter, accordingly they are able to form inclusion complex with the most diverse kinds of compounds but the inclusion complexes of the same compound formed with the different kinds of cyclodextrin have very different properties. There is a possibility to carry out further modifications in the cyclodextrin molecule with suitable substitutions. For example in case of dimethyl-β-cyclodextrin (DIMEB) two hydroxyl groups of every glucose unit are methylated, while in case of trimethyl-cyclodextrin (TRIMEB) all hydroxy groups are substituted by methoxy. The solubility of these compounds is even greater and their complex-forming capacity also differs from that of the unsubstituted cyclodextrin.

It is generally characteristic of the cyclodextrine that the external surface of the molecule is hydrophilic but the surface is apolar and due to the size of the external spaces it is capable of including—to suitable guest molecules. The so-called "molecular capsulating" can be realized in this way.

Evidence of the formation of inclusion complex between Ipriflavon and cyclodextrin is that the cyclodextrin increases the solubility of Ipriflavon in aqueous solutions. In order to determine this property, 10 mg of Ipriflavon, cyclodextrin in different amounts and 5 ml of distilled water were charged into 10 ml test tubes. After closing, the tubes were agitated for 4 days at 25° C. at 325 rpm, thereafter the samples were filtered on a G4 glass-filter and the filtrates were photometrically analyzed in 50% aqueous ethanol solution. The results are shown in Table I.

TABLE I

| Cyclodextrin mg/ml | α-CD | β-CD | γ-CD | DIMEB | TRIMEB |
|---|---|---|---|---|---|
| 1 | | 2.52 | | | |
| 3 | | 7.03 | | 22.0 | |
| 5 | | 11.44 | | 40.6 | |
| 7 | | 15.93 | | 59.1 | |
| 9 | | 19.51 | | 77.5 | |

Solubility of Ipriflavon in μg/ml determined at 25° C. in different cyclodextrin solutions of different concentration

TABLE I-continued

Solubility of Ipriflavon in μg/ml determined at 25° C. in different cyclodextrin solutions of different concentration

| Cyclodextrin mg/ml | α-CD | β-CD | γ-CD | DIMEB | TRIMEB |
|---|---|---|---|---|---|
| 11 | 4.12 | 15.22 | 2.02 | 96.2 | 8.23 |
| 13 | 4.68 | 15.48 | 2.05 | 114.8 | 9.88 |
| 15 | 5.08 | 15.75 | 2.16 | 191.3 | 11.32 |
| 20 | 6.10 | 13.46 | 2.38 | 284.4 | 14.71 |
| 30 | 8.19 | 7.59 | 2.74 | 416.8 | 26.82 |
| 40 | 9.63 | 6.20 | 3.26 | 588.2 | 43.91 |
| 50 | 10.61 | 5.44 | 3.04 | 761.0 | 61.3 |
| 70 | 14.77 | 6.08 | 3.64 | 1118 | 96.2 |
| 90 | 18.24 | 6.93 | 4.51 | 1142 | 127.5 |
| 100 | 21.63 | 6.64 | 4.76 | 1654 | 179.0 |
| 110 | 19.02 | 5.98 | 5.12 | 1824 | 218.8 |
| 120 | 23.65 | 5.66 | 5.48 | 2012 | 269.3 |
| 150 | | | | 2024 | 435.6 |

The solubility of Ipriflavon in distilled water is 1-2 μg/ml at 25° C. As it is evident from the data of Table I the solubility of Ipriflavon can increase in β-cyclodextrin solution—depending on the concentration of the β-cyclodextrin—up to the 15-fold of the solubility measured in distilled water. Increasing the β-cyclodextrin concentration up to 1%, the solubility of the Ipriflavon increases about up to 16–20 μg/ml but upon further increasing the cyclodextrin concentration the solubility value remains first constant then it begins to decrease when the cyclodextrin concentration exceeds the value of 1.8%. The solubility reaches the constant value of 6 μg/ml when the cyclodextrin concentration exceeds the 4% in the suspension. This value can be regarded as the solubility limit of the solid inclusion complex formed in the presence of the excess of Ipriflavon.

In γ-cyclodextrin solution the solubility does not increase considerably, only a 3-fold increase can be achieved.

In case of α-cyclodextrin the solubility of Ipriflavon increases up to the value 20–22 μg/ml in a 12% solution and surprisingly the UV spectrum of Ipriflavon changes in such solution as well.

Using TRIMEB or DIMEB, a still greater increase of solubility can be observed. Increasing the concentration of cyclodextrin, derivatives the increase of the solubility of Ipriflavon is almost linear. In a 15% solution of TRIMEB a solubility of 440 μg/ml and in a 15% solution of DIMEB a solubility of 1700–2000 μg/ml can be achieved, corresponding to a 300-fold and a 1770-fold increases of solubility, respectivelly.

Summarizing the aforementioned results, the solubility of the Ipriflavon inclusion complex according to the invention is 4-fold greater—related to the active ingredient—than that of the Ipriflavon per se, and the resorption thereof after oral administration to the rats is minimum 10-fold better as compared to the blood level measured after the administration of the free active ingredient in the same dose. The unchanged 7-isopropoxy-isoflavone-level is at least 25% of the total resorptionable material.

The inclusion complex according to the invention can be prepared when 7-isopropoxy-isoflavone is reacted with any cyclodextrin derivative in aqueous—organic solvent medium. As organic solvent an alcohol or ketone can be used. Preferably, the aqueous ethanol solutions of the components are reacted—preferably at 50% ethanol concentration—then the crystalline product obtained is isolated by cooling.

According to an alternative method, the two components can be kneaded in aqueous acetone medium simultaneously with the evaporation of the solvent. Using DIMEB or TRIMEB or soluble cyclodextrin polymer, the solid, power-like product can be isolated from the reaction mixture by evaporation, spray-drying, freeze-drying or in case of DIMEB by heating the solution.

In the following non-limiting Examples the invention is illustrated in detail.

Examples for the preparation of cyclodextrin-Ipriflavon inclusion complexes:

Example 1

Preparation of Ipriflavon-β-cyclodextrin inclusion complex having a molar ratio of 1:2

11.0 g (39.2 mmoles) of Ipriflavon and 114.3 g (88.3 mmoles) of β-cyclodextrin of 12.36% moisture content, were dissolved in 2.25 liters of 50% by volume aqueous ethanol solution at 80° C. under vigorous stirring and left to cool to room temperature. The crystalline product precipitated was filtered and dried for 24 hours at 60° C. to give 96.4 g of product in form of loose, white powder. The particle size is smaller than 90 μm. Ipriflavon content: 10.8% by weight; Ipriflavon: -β-cyclodextrin ratio=1:2; Yield related to the active ingredient: 94.7%.

To provide that the above product is really an inclusion complex, different thermoanalytical, X-ray diffraction and dissolution analysises have been carried out.

The thermoanalitical behaviors of the mechanical mixture and the free components are almost the same, but changes in the complex due to heating can only be observed simultaneously with the decomposition of the cyclodextrin. Testing the mechanical mixture with differential scanning calorimetry (DSC) at 115° C. an endothermic peak appears corresponding to the melting point of Ipriflavon, but no peak can be observed in case of the complex. The mechanical mixture show an continuous mass-loss—according to their Ipriflavon content—between 130° C. and 250° C., but in case of complexes no mass-loss or releasing of organic substance can be observed in the same temperature interval (Thermal Evolution Analysis, TEA).

The X-ray diffraction powder diagram of the mechanical mixture consists of the additive sum of the powder diagrams of the components. However, the powder diagram of the complex contains less peaks and new peaks (2 θ°=6.7; 7.8; 20.9) being characteristic for the complex and different from the characeteristic peaks of the β-cyclodextrin (2 θ°=4.5; 10.6; 12.3) and Ipriflavon appear (2 θ°=5.8; 11.5; 15.5; 17.3; 22.0), proving a new crystalline structure and so verifying indirectly the formation of the inclusion complex.

To carry out the dissolution tests 250 ml of distilled water were charged into a 500 ml flask and heated to 37° C. Thereafter the product in an amount corresponding to 50 mg of active ingredient was added then the suspension thus obtained was stirred at 1000 rpm using a magnetic stirrer. At fixed intervals 2–6 ml of samples were taken and filtered on glass-filter and after diluting, the filtrates were measured photometrically in an 1:1 mixture of water:ethanol.

The results obtained are summarized in Table II.

TABLE II

Dissolution of Ipriflavon, Ipriflavon-β-cyclodextrin inclusion complex prepared according to Example 1 and mixture of Ipriflavon and β-cyclodextrin in 250 ml of distilled water at 37° C.

| | Concentration of dissolved Ipriflavon μg/ml | | |
|---|---|---|---|
| Time (min) | Ipriflavon 51.5 mg | Ipriflavon-β-cyclo-dextrin inclusion complex 471.5 mg | Ipriflavon (50.5 mg) + cyclodextrin (444.7 mg) |
| 1 | 0.435 | 13.21 | 0.442 |
| 2 | 0.327 | 9.26 | 0.462 |
| 3 | 0.401 | 8.03 | 0.726 |
| 5 | 0.507 | 7.62 | 1.20 |
| 10 | 0.882 | 7.62 | 2.28 |
| 15 | 1.123 | 7.43 | 3.21 |
| 20 | 1.197 | 7.89 | 4.69 |
| 30 | 1.423 | 6.89 | 5.86 |
| 40 | 1.508 | 7.11 | 6.07 |
| 60 | 1.621 | 6.81 | 6.27 |
| 90 | 1.525 | 6.89 | 6.34 |
| 120 | 1.482 | 6.94 | 6.37 |

The dissolution of the free active ingredient is relative slow, it reaches the saturation value of Ipriflavon (about 1.5 μg/ml) after 40–50 minutes. In case of samples containing Ipriflavon-β-cyclodextrin complex, the maximum concentration of the dissolved Ipriflavon is already obtained after 1 minute, i.e. the active ingredient dissolves at once—also a flash-dissolution proceeds—, moreover at the beginning the concentration of the active ingredient may be as high as the double of the saturation value. The dissolution of the mixture of Ipriflavon and β-cyclodextrin is slower, the concentration of the dissolved active ingredient approaches the value, determined when the inclusion complex was dissolved, only after 30–40 minutes.

The dissolution of the active ingredient have been determined at different pH value as well. The dissolution curves obtained at pH=1.3 (it corresponds to the gastric activity; HCl) and at pH=7.6 (corresponding to the intestinal pH value; phosphate buffer) do not differ significantly from the dissolution values obtained in distilled water, accordingly the dissolution of the active ingredient is independent of the pH in the tested pH range.

Example 2

Preparation of Ipriflavon-γ-cyclodextrin inclusion complex having a molar ratio of 1:2

0.5 g (1.78 mmoles) of Ipriflavon were dissolved in 50 ml of 96% ethanol and the solutions thus obtained was added dropwise to the solution of 8.0 g (5.35 mmoles) of γ-cyclodextrin of 13.3% moisture content in 50 ml of distilled water, during 2 hours, then the mixture left to cool to room temperature. After a further 16-hour intensive stirring the product obtained was filtered and dried for 24 hours at 60° C. to give 5.5 g of product. Ipriflavon content: 7.9% by weight, molar ratio of Ipriflavon:γ-cyclodextrin=1:2.29. Yield related to the active ingredient: 87%. The product also contains free cyclodextrin.

Example 3

Preparation of Ipriflavon-γ-cyclodextrin inclusion complex having a molar ratio of 1:2

0.5 g (1.78 mmoles) of Ipriflavon were dissolved in 10 ml of acetone in pulg mortar and 4.0 g (3.70 mmoles) of γ-cyclodextrin of 10% by weight moisture content and 2 ml of distilled water were added. The light suspension thus obtained was homogenized with a standing rubbing until the solvent was evaporated. Thereafter the product thus obtained was dried for 24 hours at 60° C. It contains 11.1% of active ingredient and also free γ-cyclodextrin. Molar ratio of Ipriflavon to α-cyclodextrin=1:2.1.

Formulation examples for pharmaceutical compositons containing Ipriflavon—cyclodextrin inclusion complexes as active ingredients and biological tests thereof

Example 4

The dissolution properties of the known Yambolap tablet containing 200 mg of Ipriflavon (A), tablet containing 40 mg Ipriflavon in form of β-cyclodextrin inclusion complex prepared according to Example 1(B) and tablet containing the mixture of 200 mg of Ipriflavon and 330 mg of β-cyclodextrin were compared at 37° C. in 500 ml of gastric juice using Erweka ZT-4 equipment. One piece of tablet was placed into the equipment and the amount of the dissolved material was determined spectrophotometrically at 247 nm.

The compositions of the tested tablets were the following:

Table A (known tablet Yambolap, K-020484):

| Ipriflavon | 200 mg |
|---|---|
| Amylum maxdis | 36 mg |
| Lactosum | 60 mg |
| PVP | 13 mg |
| Esma Spreng | 30 mg |
| Talcum | 7 mg |
| Magnesium stearinicum | 4 mg |
| | 350 mg |

Tablet B:

| Inclusion complex according to the invention containing 40 mg of Ipriflavon | 370 mg |
|---|---|
| PVP | 15 mg |
| | 385 mg |

Tablet C:

| Ipriflavon | 200 mg |
|---|---|
| β-cyclodextrin | 330 mg |
| PVP | 20 mg |
| | 550 mg |

The results of the dissolution tests are summarized in Table III.

TABLE III

Amounts of the active ingredient dissolved from the different tablets

| Time (min) | Amounts of the dissolved active ingredient (mg) | | |
|---|---|---|---|
| | A | B | C |
| 2 | — | 0.80 | — |
| 5 | 0.21 | 1.05 | 0.27 |
| 10 | 0.45 | 1.10 | 0.50 |
| 15 | 0.58 | 1.15 | 0.60 |
| 30 | 0.56 | 1.15 | 0.65 |
| 60 | 0.61 | 1.30 | 0.75 |
| 120 | 0.60 | 1.30 | 1.00 |

TABLE III-continued

| Amounts of the active ingredient dissolved from the different tablets | | | |
|---|---|---|---|
| Time (min) | Amounts of the dissolved active ingredient (mg) | | |
| | A | B | C |
| 180 | 0.62 | 1.40 | 1.15 |

The results show that only 0.62 mg of Ipriflavon dissolves out from the conventional tablet but in case of a tablet containing one-fift of active ingredient in form of β-cyclodextrin inclusion complex compared to the amount of the active ingredient being in the conventional tablet, the quantity of the dissolved active ingredient doubles and the amount of the dissolved material exceeds with 30% of the maximum value obtained by the conventional tablets after 2 minutes. In case of a tablet which contains the Ipriflavon and β-cyclodextrin in form of mechanical mixture, the dissolution was somewhat slower but even so, the quantity of the dissolved active ingredient was higher as compared to the conventional tablet.

To the resorption tests CFY male rats weighing 170–200 g were used. After a 16-hour fasting period, Ipriflavon in a dose of 25 mg/kg (group A), Ipriflavon—-β-cyclodextrin inclusion complex prepared according to Example 1 (group B) and Ipriflavon-β-cyclodextrin mixture (group C)—both containing the β-cyclodextrin in equimolar ratio to the active ingredient—were administered, thereafter rat-food and water were given "ad libitum" to the animals.

The materials to be tested were mixed for 5 minutes in 2 ml of 1% methylcellulose solution and administered by the aid of a stomach tube. The plasma samples were collected 10, 30 minutes and 1, 2 and 4 hours after the treatment using mortal haemorrhage after transecting the Vena femoralis of the animals anesthetized with ether. The blood samples were charged into heparinized tubes, centrifuged, nutsch-filtered and stored deep-frozen, in vials until further use.

In order to collect urinary samples, after treatment the animals were placed into individual metabolism vessel and urine and faeces were separately collected for 24 hours. The urinary samples were stored deep-freezed until further use. The concentration of the unchanged Ipriflavone and its main metabolite (7-hydroxy-isoflavon) in the urinary and the plasma samples was followed by HPLC.

To carry out the HPLC, liquid chromatography of typ RP-18 and LiChrosorb reverse phase column (grain size in case of plasma sample: 10 μm and in case of urinary samples: 5 μm) were used. Flow velocity of eluent: 1.5 ml/min, wave length of UV detector: 254 nm, paper-velocity: 0.2 cm/min.

In case of plasma samples a mixture of 0.05M acetate buffer (pH=3):acetonitrile=60:40 and in case of urinary samples a mixture of acetate buffer:acetonitrile=55:45 were used as eluent. The internal standard was ethanolic solution of 2-methyl-7-methoxy-4'-nitro-isoflavone (100 μg/ml) and to the calibration, solutions comprising 100 μg/ml and 10 μg/ml of 7-hydroxy-isoflavone in methanol were used.

To analyze the plasma samples, to 1 ml of plasma 1 ml acetate-buffer (pH=5) and β-glucuronidase (arylsulfonase) enzyme (100 FU) diluted to 10-fold with 10 μl of distilled water were added and incubated at 37° C. for 24 hours. After incubation, 50 μl of 2N NaOH were added and the mixture was extracted with benzene and centrifuged. The organic phase was separated, the aqueous phase was made acidic with 400 ml of 1N HCl, and after adding 50 μl of internal standard solution it was repeatedly extracted with 8 ml benzene. The organic phase was centrifuged, evaporated, the residue was dissolved in 100 μl of eluent and 50 μl of this solution were injected and measured.

Equation of the calibration curve: $y=8.2x-0.08$; correlation coefficient: 0.9999.

To analyse the urinary sample, to 0.5 ml of urine 0.5 ml of acetate buffer (pH=5) and 10 μl of β-glucuronidase (arylsulfatase) enzyme (1000 FU) were added and the mixture was extracted with 8 ml of benzene and centrifuged. The organic phase was separated, the aqueous phase was acidified with 400 ml of 1N HCl, and after adding B 50 μl of internal standard solution it was extracted with further 8 ml of benzene. The organic phase was centrifuged, evaporated, the residue was dissolved in 100 μl of eluent, and 10 μl of this solution were injected into the liquid chromatograph.

Equation of the calibration curve: $y=0.911x-0.09$, correlation coefficient: 0.9995.

In Table IV the concentration values of unchanged Ipriflavon and in Table V the concentration values of the main metabolite determined in the blood of animals are shown. To group A Ipriflavon per se, to group B the inclusion complex according to the invention and to group C the mixture of Ipriflavon and β-cyclodextrin were administered.

TABLE IV

| Plasma-level values in μg/ml of unchanged Ipriflavon as a function of time after p.o. administration of equivalent doses | | | |
|---|---|---|---|
| Time (h) | A Ipriflavon | B Inclusion complex prepared acc. to Example 1 | C Mixture of Ipriflavon and β-cyclodextrin |
| 0.17 | 0 | 0.065 | 0.479 |
|  | 0 | 0.055 | 0 |
|  | 0 | 0.073 | 0 |
| 0.5 | 0 | 0.468 | 0 |
|  | 0 | 0.149 | 0 |
|  | 0 | 0.194 | 0 |
| 1 | 0 | 0.271 | 0 |
|  | 0 | 0.354 | 0 |
|  | 0 | 0.293 | 0 |
| 2 | 0.078 | 0.514 | 0.081 |
|  | 0 | 0.402 | 0 |
|  | 0.095 | 0.214 | 0 |
| 4 | 0.041 | 0.148 | 0 |
|  | 0 | 0.363 | 0 |
|  | 0 | 0.054 | 0 |
| 24 | 0 | 0 | 0 |
|  | 0 | 0 | 0 |
|  | 0 | 0 | 0 |

TABLE V

| Plasma-level values of μg/ml of main metabolite (7-hydroxy-isoflavone) as a function of time after p.o. administration of equivalent doses | | | |
|---|---|---|---|
| Time (h) | A Ipriflavon | B Inclusion complex prepared acc. to Example 1 | C Mixture of Ipriflavon and β-cyclodextrin |
| 0.17 | 0.156 | — | 2.080 |
|  | 0.265 | 2.450 | 0.457 |
|  | 0.195 | 3.650 | 0.767 |
| 0.5 | 0.860 | 12.270 | 0.304 |
|  | 0.591 | 4.840 | 0.374 |
|  | 0.365 | — | 0.358 |
| 1 | 0.239 | 12.190 | 0.306 |
|  | 0.790 | 4.330 | — |

TABLE V-continued

Plasma-level values of µg/ml of main metabolite (7-hydroxy-isoflavone) as a function of time after p.o. administration of equivalent doses

| Time (h) | A Ipriflavon | B Inclusion complex prepared acc. to Example 1 | C Mixture of Ipriflavon and β-cyclodextrin |
|---|---|---|---|
|  | 0.340 | 3.870 | 0.274 |
| 2 | 1.218 | 22.040 | 0.270 |
|  | 0.715 | — | 0.358 |
|  | 1.093 | 3.780 | 0.826 |
| 4 | 0.220 | 1.740 | — |
|  | 0.237 | — | 0.130 |
|  | 0.235 | 2.520 | 0.330 |
| 24 | 0 | 0 | 0 |
|  | 0 | 0 | 0 |
|  | 0 | 0 | 0 |

In every period, unchanged Ipriflavon can be detected only in case of group B and it amounts to 50–500 ng/ml. In case of group A similarly to group C, unchanged Ipriflavon can be detected only in few periods (at 2 and 4 hours). As to the main metabolite in every period the plasma levels were 10–20-fold higher in group B as compared to that of groups A and C determined in the same period, i.e. the values of group B are between 3–20 µg/ml while in case of groups A and C they are between 0.2–1.0 µg/ml. In all cases a second peak appears in the plasma curve at the 2-hour period which may be the result of an intensive enterohepatitic cycle and a more better resorption from the small intestine.

In Table VI the results of the HPLC analysis of urinary samples are shown. In the 0–24 hour urinary samples no unchanged Ipriflavon can be detected. However, the main metabolite (in all cases) can be followed. The average value of 7-hydroxy-isoflavone were 952 µg corresponding to a 3-fold increase as compared to the other groups. According to our experience the quantity of the main metabolite is 50–55% of the total quantity of the metabolite and so the total quantity discharged with urine is 2-fold higher than the quantity determined by us de facto. Upon this consideration in case of group B and 40%, while in case of groups A and C only 10–14% of the dose administered are discharged with the urine.

According to the aforementioned facts it can be proved that after administration of Ipriflavon-β-cyclodextrin inclusion complex to rats a 10–15-fold increase of plasma-level and about 3-fold higher quantity of substance discharged with urine can be achieved as compared to the control.

TABLE VI

Amounts of main metabolite (7-hydroxy-isoflavone) discharged with urine, measured after the p.o. administration of equivalent doses

|  | No. of animals | Total amounts of material discharged µg | Amounts of the material discharged, in % of the doses D % | D % |
|---|---|---|---|---|
| A Ipriflavon | 1 | 236.1 | 9.44 | 11.34 |
|  | 2 | 344.4 | 13.77 |  |
|  | 3 | 270.4 | 10.81 |  |
| B Inclusion complex acc. to Example 1 | 4 | 925.4 | 37.01 | 38.09 |
|  | 5 | 978.9 | 39.16 |  |
| C Mixture of Ipriflavon and β-cyclodextrin | 6 | 341.6 | 13.66 | 13.33 |
|  | 7 | 494.3 | 19.77 |  |
|  | 8 | 163.9 | 6.56 |  |

What we claim is:

1. The inclusion complex of 7-isopropoxy-isoflavone formed with heptakis-2,6-O-dimethyl-β-cyclodextrin.

* * * * *